(12) United States Patent  
Aschmann

(10) Patent No.: US 8,114,078 B2
(45) Date of Patent: Feb. 14, 2012

(54) INTRAMEDULLARY NAIL FOR FEMUR FRACTURE FIXATION

(75) Inventor: Felix Aschmann, Basel (CH)

(73) Assignee: Synthes USA, LLC, West Chester, PA (US)

(*) Notice: Subject to any disclaimer, the term of this patent is extended or adjusted under 35 U.S.C. 154(b) by 1301 days.

(21) Appl. No.: 11/247,560

(22) Filed: Oct. 10, 2005

(65) Prior Publication Data

US 2006/0084999 A1    Apr. 20, 2006

Related U.S. Application Data

(63) Continuation of application No. PCT/IB2004/001064, filed on Apr. 7, 2004.

(51) Int. Cl.
*A61B 17/72* (2006.01)
(52) U.S. Cl. ............................ 606/64; 606/66
(58) Field of Classification Search ............ 606/62–68, 606/96, 98, 329; 623/23.23
See application file for complete search history.

(56) References Cited

U.S. PATENT DOCUMENTS

| | | | | |
|---|---|---|---|---|
| 3,530,854 A * | 9/1970 | Kearney | .................. | 606/67 |
| 4,432,358 A * | 2/1984 | Fixel | .................. | 606/66 |
| 4,494,535 A * | 1/1985 | Haig | .................. | 606/67 |
| 4,657,001 A * | 4/1987 | Fixel | .................. | 606/66 |
| 5,087,260 A * | 2/1992 | Fixel | .................. | 606/65 |
| 5,454,813 A * | 10/1995 | Lawes | .................. | 606/62 |
| 5,534,004 A * | 7/1996 | Santangelo | .................. | 606/68 |
| 6,077,264 A | 6/2000 | Chemello | | |
| 6,168,595 B1 * | 1/2001 | Durham et al. | .................. | 606/64 |
| 6,261,290 B1 | 7/2001 | Friedl | | |
| 6,423,066 B1 * | 7/2002 | Harder et al. | .................. | 606/65 |
| 6,524,314 B1 * | 2/2003 | Dean et al. | .................. | 606/64 |
| 2002/0045900 A1 | 4/2002 | Harder et al. | | |

FOREIGN PATENT DOCUMENTS

EP    257 118 A1    3/1988
EP    1016382 A2 *    7/2000

OTHER PUBLICATIONS

"Notch," Compact Oxford English Dictionary. Oxford University Press, 2010. accessed Mar. 29, 2010. http://www.askoxford.com/concise_oed/notch?view=uk.*

* cited by examiner

*Primary Examiner* — Eduardo C Robert
*Assistant Examiner* — Steven Cotroneo
(74) *Attorney, Agent, or Firm* — Kay Kaplun & Marcin, LLP

(57) ABSTRACT

An intramedullary nail for the fixation of fractures of the proximal femur, with a femur neck screw (10a), installable with a proximal femur nail (1a), into the intramedullary area, by a diagonal bore (7a), running to the longitudinal axis of the femur nail (1a), from the side of the femur nail (1a), and a locking element (16a) with at least one prong (18a) parallel to the axis of the femur neck screw (10a). A positive connection between the locking element (16a) and a groove (8a) in the bore (7a) of the femur nail (1a) forms a twisting lock of the femur neck screw (10a) and, allows for the axial movement of the femur neck screw (10a) in the bore (7a) of the femur nail (1a).

18 Claims, 6 Drawing Sheets

INTRAMEDULLARY NAIL FOR FEMUR FRACTURE FIXATION

CROSS REFERENCE TO RELATED APPLICATION

This application is a continuation of International Patent Application No. PCT/IB2004/001064, filed Apr. 7, 2004, the entire contents of which is expressly incorporated herein by reference. The International Patent Application No. PCT/IB2004/001064 claims priority from Swiss Application No. 2003 0648/03, filed Apr. 9, 2003.

TECHNICAL FIELD

The present invention relates generally to an intramedullary nail for femur fracture fixation.

BACKGROUND OF THE INVENTION

It is known in the art to use screws and blades as fastening parts, and in particular the so-called spiral blades. Screws provide an excellent grip in the axial direction, a moderate grip in the radial direction (perpendicular to the screw axis), and almost no grip against rotation around the screw axis. Opposing blades provide a very good grip in radial direction as well as against rotation around the blade axis, but almost no grip in the axial direction.

It is also well-known to use intramedullary nails in the healing process of fractured or broken bones in the jaw or the infra-cervical area (see European document EP-A-257 118). The intramedullary nails comprise a femur nail with bone screws running crosswise to it. The femur nail is relatively resistant to bending and fills up almost the entire intramedullary area of a bone. The femur nail contains several cross holes. By using bone screws (i.e., "locks") on both sides of the fracture, the femur nail is firmly embodied in the bone. Upon installation of a intramedullary nail the bone becomes strong again within a short time. The proximal area of the femur nail is equipped with a diagonal hole, through which femur neck screws are passed. A twist lock of the femur neck screw is provided in the diagonal perforation, permitting the axial movement of the femur neck screw. This twist lock is achieved by the action of bolting device nails on the femur neck screw in the diagonal perforation area, forming several parallel axes within equidistant slots in a circumferential direction, into which the proximal end femur nails are inserted, themselves extending to these coaxes. The slots permit axial movement of the femur neck screw (transverse to the femur nail). The lock nail intervening in each of the slots prevents inadvertent rotation of the femur neck screw.

While the bone heals, a so-called narrowing frequently occurs whereby the bone shortens within the fracture area. If the femur neck screw does not stop this shortening, there may be a danger of the femur neck screw breaking through the femur head or of the fracture becoming unstable.

There exist various other constructional possibilities to secure the femur neck screw in the direction of rotation and to permit an axial movement at the same time. Such a femur neck screw is thus secured against rotation opposite the femur nail, but the proximal bone fragment can still rotate inversely to the femur neck screw around its axis.

A solution is known from the U.S. Patent Publication No. US2002/0045900 (Harder et al.), where a femur neck screw has two diametrically opposed longitudinal slots into which an essentially u-shaped locking element is pushed or driven in. This solution represents a combination of screws and blades and unites the desired characteristics of both fastening parts. However, the height of the branches of the locking element is relatively small, since they are governed by the femur nail only in the femur neck screw slots, and thus their effect as blades is limited. The branches of the locking element spread themselves along the depth of the longitudinal slots reducing laterally to the screw point. The locking element only serves to prevent the projection of bone fragments from the femur neck screw. The turning lock of the femur neck screw in the femur nail takes place in a way similar to the European document EP-A-257 118 by means of a bolting device nail at the proximal end of the femur nails, inducing the need for the surgeon to work on both sides when inserting and locking the femur neck screw.

The problem of rotation is fixed by the implant system described in WO-A-01/739679 through means of two proximal fixation screws. However, such an operation is more costly and there exists a problem that with small jaw necks the two screws will hardly find any place or none at all to be secured to.

Another system uses a spiral blade as the only proximal locking element, which is secured around the axis by a rotation preventing nail. The proximal bone fragment cannot rotate anymore around the axis of the blade. In practice this means that, owing to its larger bearing surface, the blade cannot cut through the bone "laterally" under load as is the case with other screws. It is, however, unfortunate that the spiral blade does not support the femur head sufficiently in the axial direction.

The spiral blade and the screw of U.S. Patent Publication No. US2002/0045900, as mentioned earlier, must be secured against rotation around the femur nail by an additional element at the proximal end of the femur nails. A particular problem of the femur neck screw US2002/0045900 is that there is reduced sliding ability of the screw/locking element along the screw axis during the drilling in of the femur nails, since upon sinking the branches of the u-shaped locking element are spread by the nail against slots of smaller depth in the screw, and they may block themselves during the drilling in of the femur nail.

SUMMARY OF THE INVENTION

The present invention provides a remedy for the above-discussed disadvantages/problems. The objective of the invention is to provide an appropriate intramedullary nail with a proximal locking element, introduced through a single entrance and yet tightly securing the proximal bone fragment. The present invention is directed to an intramedullary nail for proximal femur fracture fixation, with a femur nail introduced from the proximal side of the intramedullary area. A femur neck screw is introduced diagonally through a lateral hole in the femur nail, running along its longitudinal axis, thus allowing a twist lock because of the possibility of axial movement of the femur neck screw in the hole of the femur nail. The femur neck screw has at least one longitudinal groove running in the axial direction and a locking element with at least one grip arranged parallel to the axis of the femur neck screw, transferable from the lateral into the longitudinal slots of the femur neck screw.

For proximal femur fractures the proximal fragment (essentially the femur head) must be correctly oriented and fixed opposite the femur shaft correctly, thus being made position and rotation-wise stable.

In one embodiment, an intramedullary nail for fixation of fractures of a proximal femur includes a femur nail and a femur neck screw. The femur nail, having a longitudinal axis, includes a proximal end having a head with a borehole running diagonal to the longitudinal axis, wherein the borehole includes one or more grooves, and a distal end having a shank with a reduced diameter with respect to the head of the proximal end, wherein the shank has a cross hole and one or more axial notches. The femur neck screw includes a cluster at a proximal end, a locking element having two or more prongs arranged almost parallel to the axis of the femur neck screw, one or more longitudinal slots oriented in an axial direction, wherein at least one prong of the locking element is inserted into one of the longitudinal slots, and a threaded end at a distal end of the femur neck screw. The femur neck screw may be inserted into the borehole of the femur nail whereby axial movement of the femur neck screw in the borehole of the femur nails is achieved making possible a twisting lock, and the twisting lock is formed by a positive connection between the locking element and the femur nail, and between the locking element and the femur neck screw.

In another embodiment, an intramedullary nail for fixation of fractures of a proximal femur includes a femur nail and a femur neck screw. The femur nail, having a longitudinal axis, includes a proximal end having a head with a borehole running diagonal to the longitudinal axis, wherein the borehole includes one groove, and a distal end having a shank with a reduced diameter with respect to the head of the proximal end, wherein the shank has a cross hole and one or more axial notches. The femur neck screw includes a cluster at a proximal end, a locking element having a first prong and two second prongs arranged almost parallel to the axis of the femur neck screw, three longitudinal slots oriented in an axial direction, wherein the three longitudinal slots are evenly spaced apart, and a threaded end at a distal end of the femur neck screw. The femur neck screw may be inserted into the borehole of the femur nail such that the first prong is situated in the groove, and the two second prongs serve only as an anti-twist plate.

In still another embodiment, an intramedullary nail for fixation of fractures of a proximal femur includes a femur nail and a femur neck screw. The femur nail, having a longitudinal axis, includes a proximal end having a head with a borehole running diagonal to the longitudinal axis, wherein the borehole includes three grooves, and a distal end having a shank with a reduced diameter with respect to the head of the proximal end, wherein the shank has a cross hole and one or more axial notches. The femur neck screw includes a cluster at a proximal end, a locking element having three prongs arranged almost parallel to the axis of the femur neck screw, three longitudinal slots oriented in an axial direction, wherein the three longitudinal slots are evenly spaced apart; and a threaded end at a distal end of the femur neck screw. The femur neck screw may be inserted into the borehole of the femur nail such that the three prongs are situated in the three grooves, thereby all three prongs provide a turning lock function of the femur neck screw.

BRIEF DESCRIPTION OF THE DRAWING

The present invention can be better understood by reference to the following drawings, wherein like reference numerals represent like elements. The drawings are merely exemplary to illustrate certain features that may be used singularly or in combination with other features and the present invention should not be limited to the embodiments shown.

DESCRIPTION OF THE PREFERRED EMBODIMENTS

Figure 1:
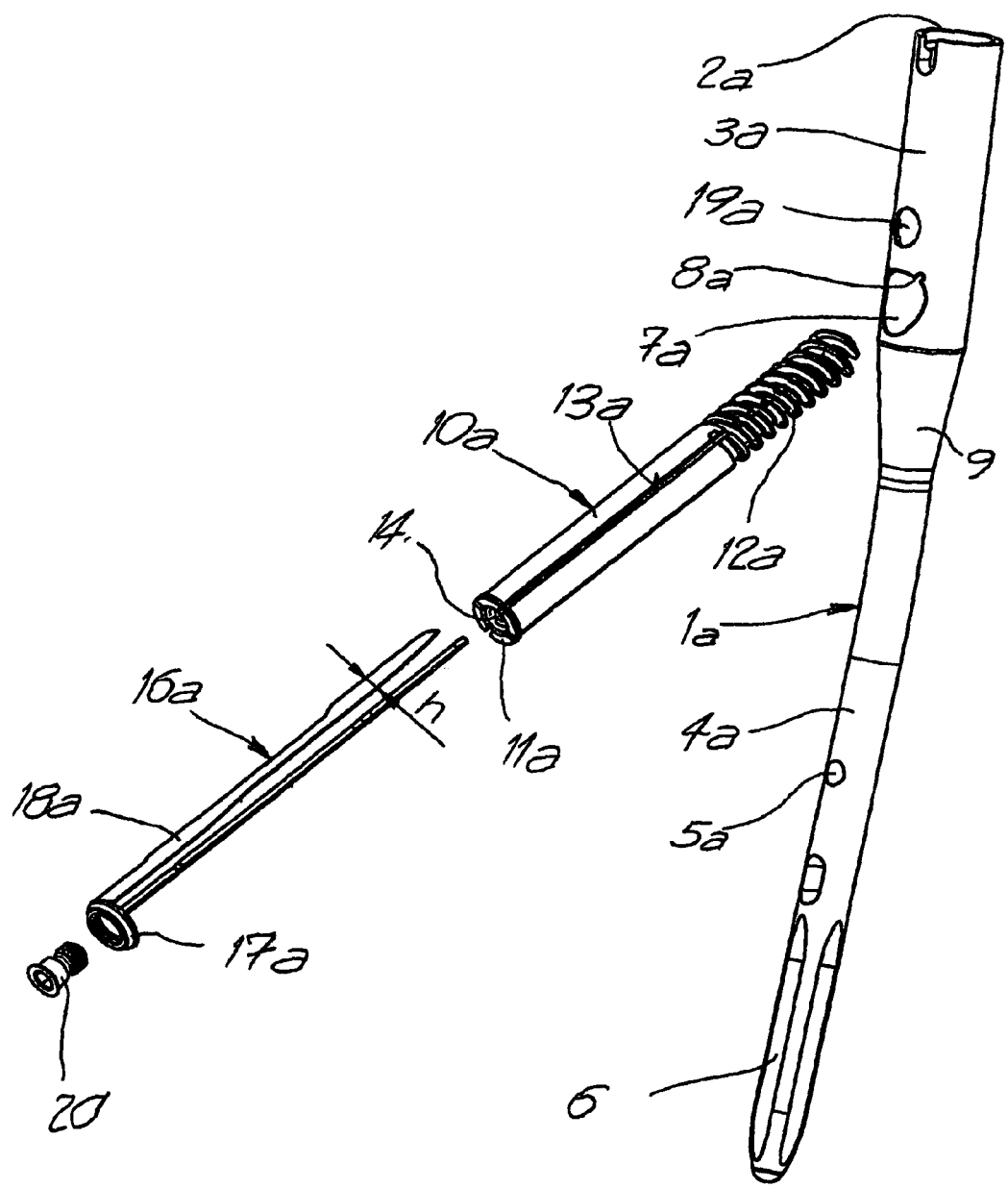
FIG. 1 is an exploded view an intramedullary nail according to the present invention with femur nail and femur neck screw.
Figure 3:
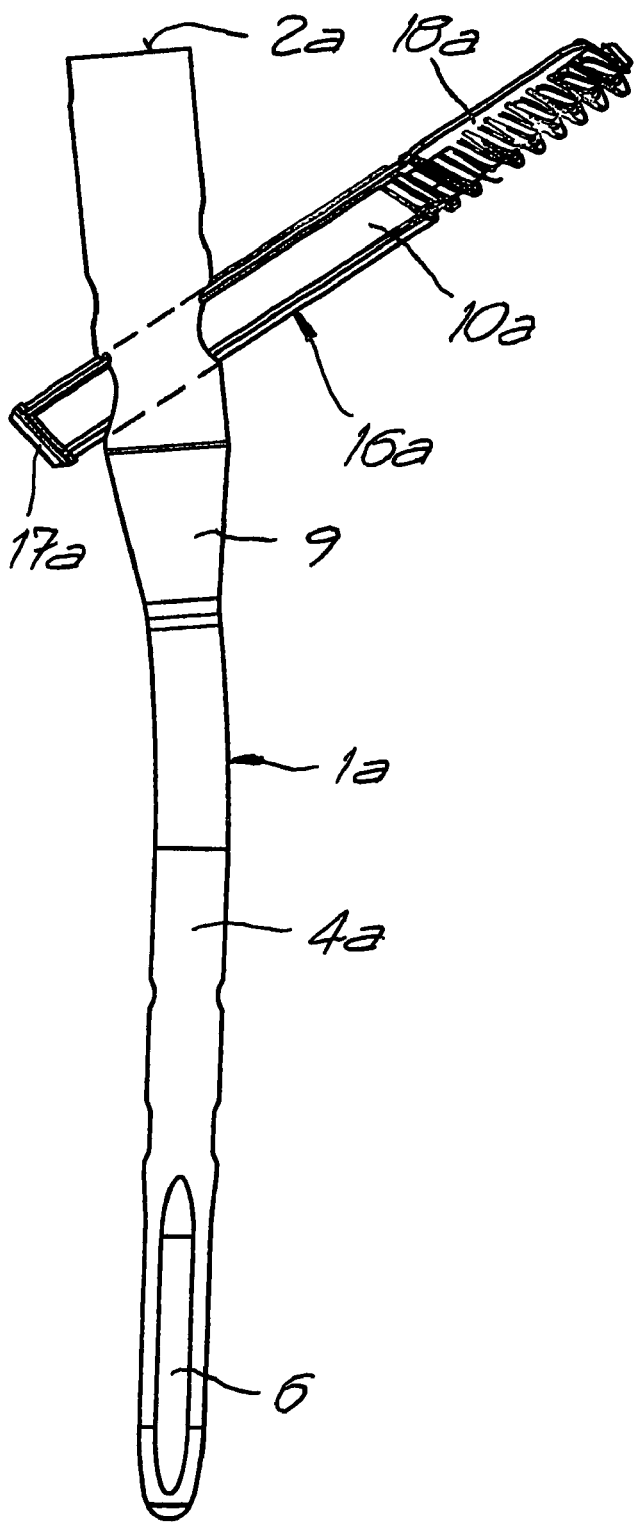
FIG. 3 is a side view of the installed intramedullary nail from FIG. 1.
Figure 2:
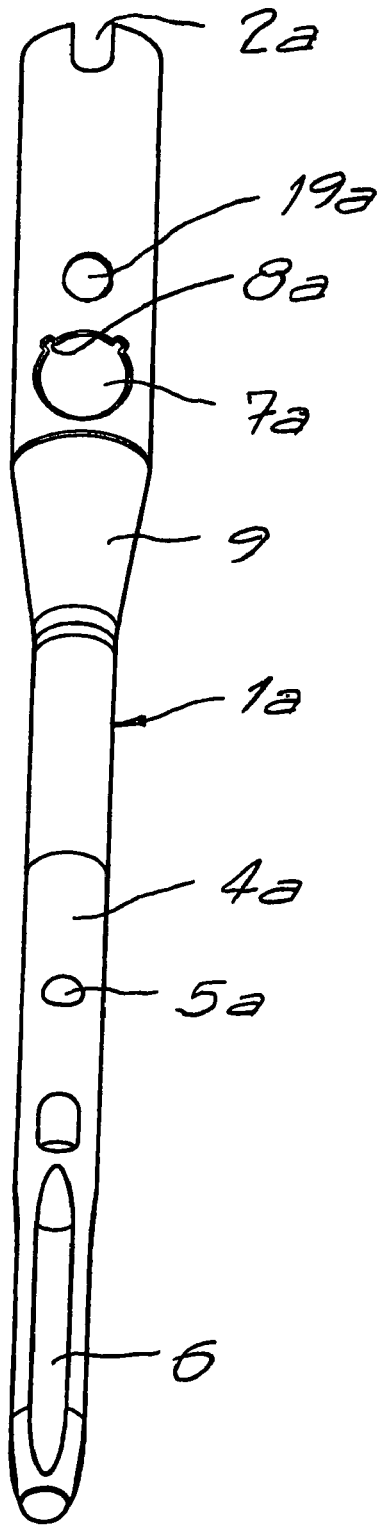
FIG. 2 is a perspective view of the femur nail from FIG. 1.

The intramedullary nail shown in FIGS. 1 to 4 essentially consists of a femur nail 1a and a femur neck screw 10a. The femur nail 1a at its proximal end 2a includes a head 3a. At the distal end, opposite the head 3a, the femur nail 1a includes a shank 4a with a reduced diameter as compared to the proximal end 2a. The transient area between head 3a and shank 4a is designed as cone 9. At the front, the shank 4a is provided with at least one cross hole 5a, which serves as an axial safety device of the femur nail 1a in the bone. In addition, shank 4a includes axial notches 6. The head 3a is provided with at least one borehole 7a, running diagonally to the longitudinal axis, and one auxiliary drilling hole 19a, running parallel to it. The borehole 7a includes at least one groove 8a. An auxiliary wire (not shown) is introduced by the auxiliary drilling 19a when pivoting the femur neck screw 10a, in order to prevent a secure driving of the bone fragment.

The femur neck screw 10a includes a cluster 11a at its proximal end. The femur neck screw 10a is provided with threads (radial screw) 12a in the direction of the front, and/or of the distal area. At the extent of the femur neck screw 10a a plurality of longitudinal slots 13a, for example four slots, are arranged. The longitudinal slots 13a have a depth which reduces towards the distal end. In the area of the cluster 11a, a tapped hole 14 is provided. After pivoting the femur neck screw 10a, a locking element 16a which includes a collar 17a, preferably circular, and a plurality of prongs 18a, for example two, spaced a distance "h" apart, is inserted in the axial direction into the longitudinal slots 13a of the femur neck screw 10a. A mounting screw 20 serves afterwards for the protection of the locking element 16a and is screwed into the tapped hole 14 of the femur neck screw 10a.

The borehole 7a also has an advantage in terms of the slots 8a running in the axial direction of the femur neck screw 10a, cooperating positively with the locking element 16a. The prongs 18a of the locking element 16a are, thus, also led through the slots 8a of the femur nail 1a, making possible an increased height of the prongs and their load-carrying capacity. As compared to the well-known u-shaped locking element, with, for example, 2 mm branch height, the height of the prongs of the present invention can be increased to at least 3 mm, which corresponds to an increase of around 50%. Such slots 8a in the borehole 7a of a femur nail 1a are relatively simple to manufacture using broaching tools.

An appropriate arrangement of the slots 8a in the borehole 7a of the femur nail 1a would be to the longitudinal slots 13a in the femur neck screw 10a. The number of slots 8a in the borehole 7a may or may not be equal to the longitudinal slots 13a in the femur neck screw 10a.

Figure 4:
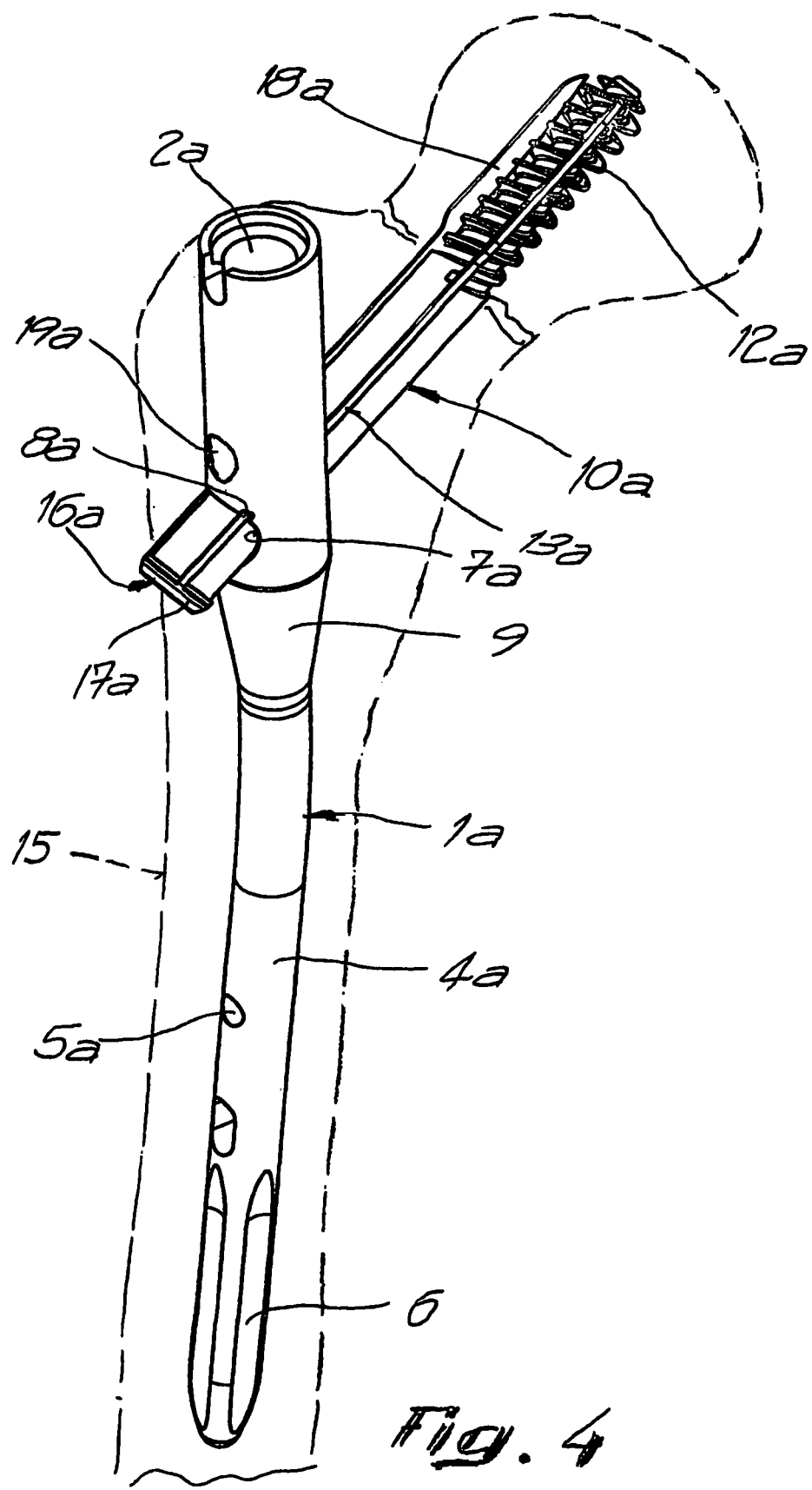
FIG. 4 is a perspective representation of the installed intramedullary nail from FIG. 3, with symbolic outlines of the surrounding bone.

FIG. 4 depicts an outline (dashed lines) of a bone 15 to be fixed by means of the intramedullary nail subject of the present invention. The prongs 18a of the locking element 16a and the longitudinal slots 13a projecting towards the distal end of the femur neck screw 10a in the distance, above the radial screw 12a are made particularly prominent. By virtue of the present invention, a turning lock of the joint ball on the femur neck screw 10a, and limited axial mobility of the femur neck screw 10a in the femur nail 1a, necessary for the healing of the bone, is achieved. In the present embodiment this is achieved because a twist lock is formed by a positive connection between the locking element and the femur nail. Thus, only one incision on the patient is needed and only laterally at the proximal end of the femur neck screw. Accordingly, an effective turning lock between the intramedullary nail 1a and the femur neck screw 10a is achieved irrespectively of how the latter is designed.

In another embodiment, the locking element 16a contains more prongs 18a than there are slots 8a in the borehole 7a in the femur nail 1a, whereby at least one jaw is governed by a groove 8a in the borehole 7a of the femur nail 1a and at least one jaw, preferably the same, is governed by a longitudinal slot 13a of the femur neck screw 10a. Thus, an anti-twist effect of the femur neck screw 10a against the femur nail 1a is produced by the locking element 16a. Such a configuration produces an advantage that the slots 8a in the femur nail 1a in an area of light pressure can be arranged to the proximal end 2a and to the distal end of the femur nail 1a. A jaw in this position, however, then only contributes to the rotational safety of the proximal fragment. The grip from the proximal end 2a to the distal nail end is established according to the positioning of prongs. These prongs are placed in areas of maximum stress on the femur nail 1a and are, therefore, governed in this example only by the longitudinal slots 13a in the femur neck screw 10a.

The depth of the longitudinal slots 13a in the femur neck screw 10a decreases, if necessary, and as with the design of the Harder et al. femur neck screw toward the distal end of the femur neck screw 10a. Thus, the prongs 18a of the locking element 16a are radially spread apart when pushing forward and an intensified turning lock of the femur neck screw 10a in the bone fragment is enabled.

Another embodiment consists in making the depth of the individual longitudinal slots 13a different. Thus the individual prongs of the locking element 16a can be more or less expanded and can, accordingly, be inserted more or less deeply into the bone segment.

The height of the locking element prongs 18a measured in the radial direction increases for the distal end of the femur neck screw 10a. This makes for a good anchorage and, thus, a particularly good turning lock of the bone fragment. The axial agility of the femur neck screw 10a can be limited by a gradated height. The axial sliding ability of the femur neck screw 10a and of the locking element 16a remains unimpaired.

In another embodiment the number of longitudinal slots 13a in the femur neck screw 10a exceed the number of prongs 18a of the locking element 16a. The locking element 16a can thus be axially inserted in different turning positions into the femur neck screw 10a and the twisting lock achieved in several locations.

In another embodiment the longitudinal slots 13a in the femur neck screw 10a and in the diagonal borehole 7a in the intramedullary nail are evenly distributed over the required extent. Thus, the locking element 16a can be introduced in arbitrary turning positions into the longitudinal slots 13a of the femur neck screw 10a. The locking element 16a may be equipped with one, two, three, four or any number of prongs, if their number and position with respect to the slots are compatible in the femur neck screw 10a and the diagonal borehole 7a. Two prongs are preferred, lying each on a separate level, diagonal to one another, so that the prongs on average look as parts of a V, a X, or a Y.

A further embodiment consists in arranging the prongs of the locking element 16a unevenly distributed over its length. So, for example, only two prongs, but multiple slots at the femur nail, and/or at the femur neck screw can be planned.

The locking element may have, if necessary, three prongs spread over approximately 120°. Three prongs provide good centering and an even force distribution over the entire length.

In order to prevent the shifting of the locking element 16a upon its introduction, an appropriate safety element is attached to the axial safety of the locking element. One embodiment consists in threading the safety element (mounting screw 20) into the proximal end of the femur neck screw of the threaded screw mountings. The safety element can, thus, be unscrewed, removed and reintroduced in the same location of the locking element.

The femur nail, the locking element, the femur neck screw and/or the safety element may consist of appropriate titanium alloys or implant steel.

Figure 5:
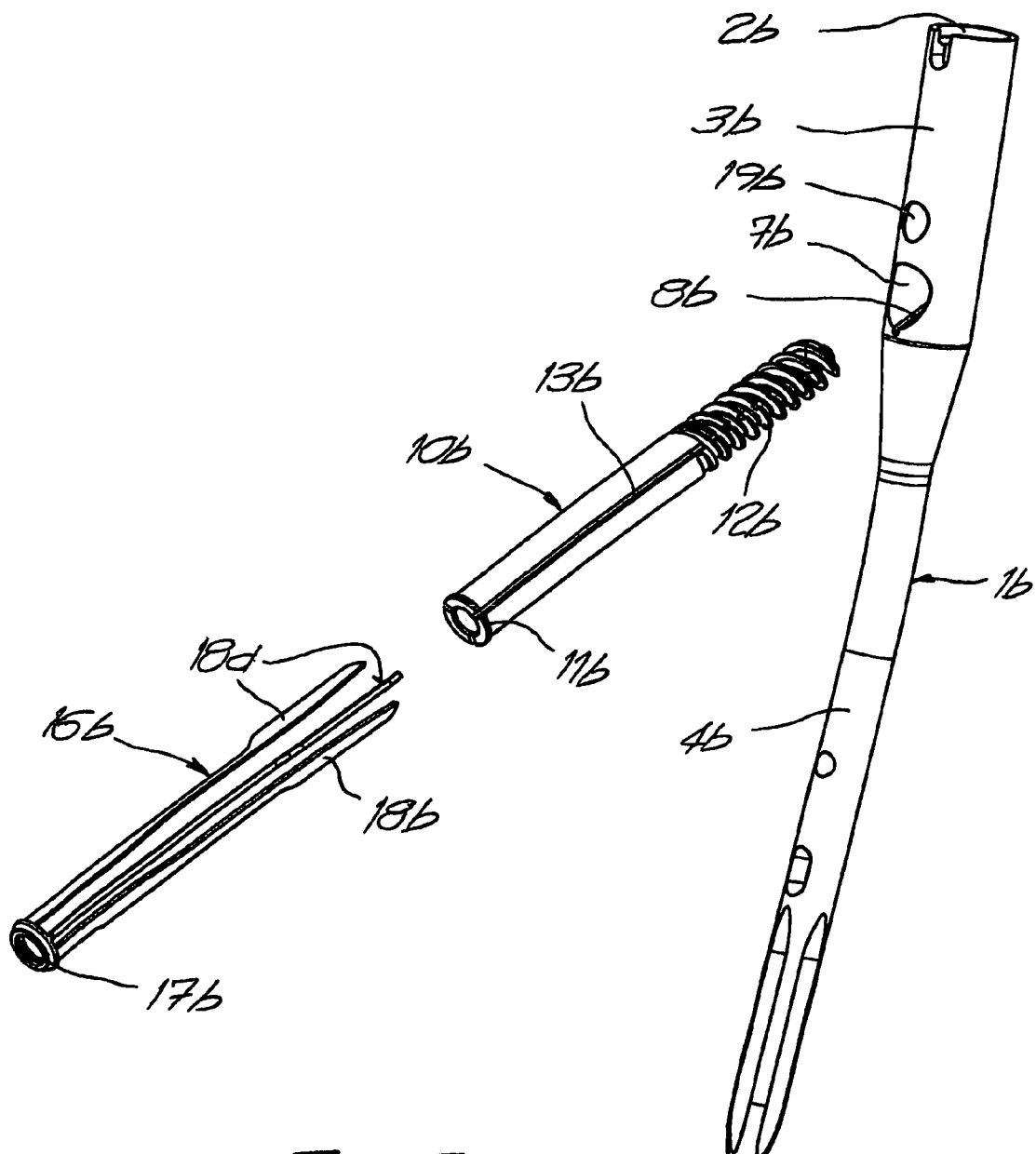
FIG. 5 is a exploded view of another exemplary embodiment.

FIG. 5 depicts a further embodiment of the intramedullary nail of the invention. In this embodiment, The embodiment depicted in FIG. 5 differs from the embodiment depicted in FIGS. 1 to 4 by the fact that the locking element 16b includes a first prong 18b and two second prongs 18d, and the femur neck screw 10b has three evenly arranged longitudinal slots 13b. The femur nail 1b, however, has only one groove 8b for turn locking the femur nail 1b penetrating femur neck screw 10b, in which rests the first prong 18b. The two second prongs 18d thus serve only as an anti-twist plate in the bone fragment. By virtue of this configuration, a different functionality may be achieved, for example, by the fact that the prongs 18b, 18d are more or less strongly expanded depending on the depth and/or form of the longitudinal slots 13b. As a variation of or in combination with this measure the height of the individual prongs 18b, 18d, measured in the radial direction, may also be different.

Figure 7:
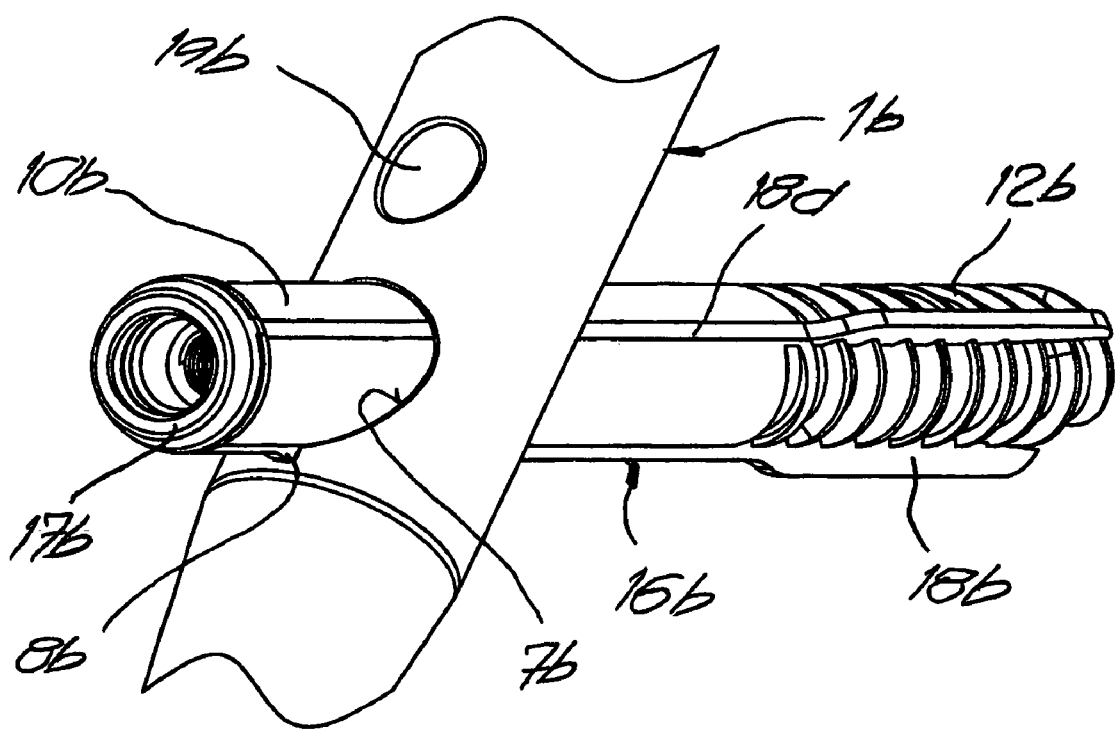
FIG. 7 is a perspective view of the installed intramedullary nail from FIG. 5.

FIG. 7 shows the femur neck screw 10b with installed locking element 16b, fitted by the femur nail 1b. The first prong 18b directed downward is more expanded than the two second prongs 18d. Thus, the rear end of the first prong 18b clearly reaches into the groove 8b in the borehole 7b of the femur nail 1b and brings about a turning lock of the femur neck screw 10b in the femur nail 1b. The two second prongs 18d do not reach above it in the expanded condition within the area of the femur nail 1b along the length of the femur neck screw 10b and stay to serve within the range of the radial screw 12b, excluding the twisting lock of the bone fragment on the femur neck screw 10b.

Figure 8:
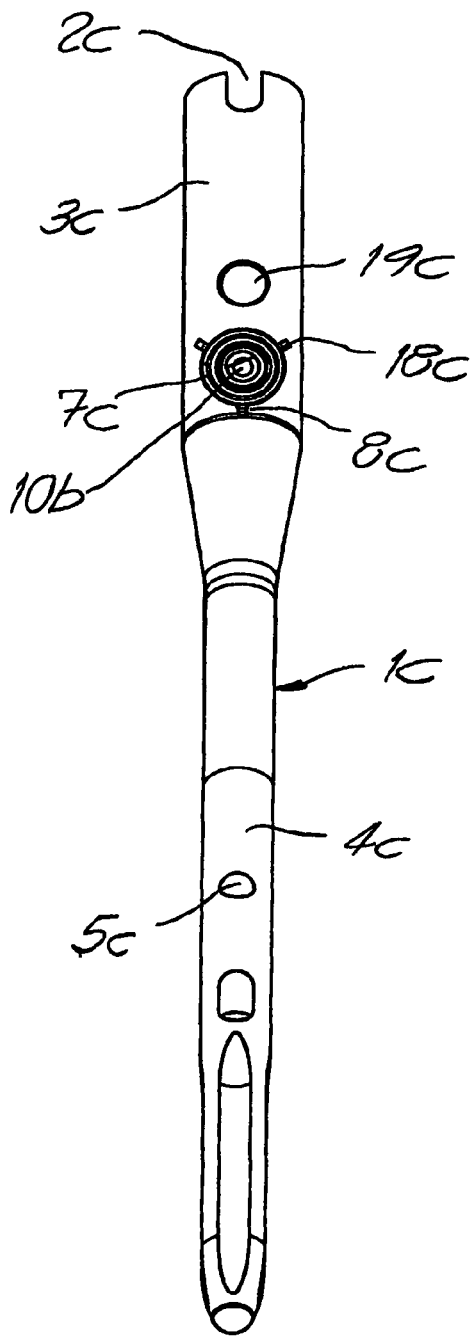
FIG. 8 is a perspective view of a further variant of the femur nail.
Figure 6:
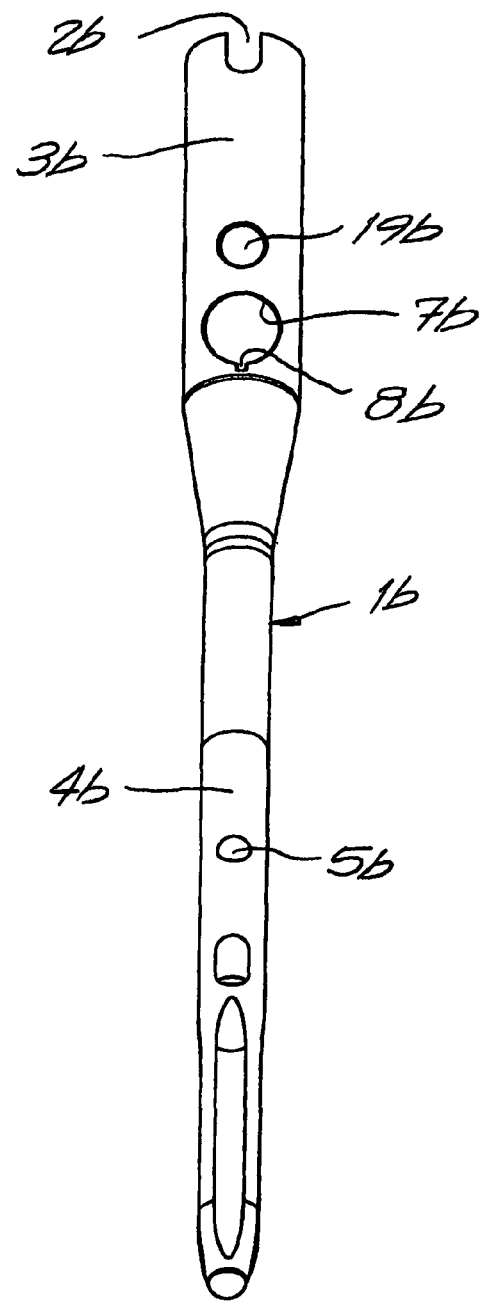
FIG. 6 is a perspective view of the femur nail from FIG. 5.

Another embodiment is depicted in FIG. 8. All three prongs 18c are radially directed, in order to be equally spaced apart when installed. The prongs 18c are merged in slots 8c of the borehole 7c of the femur nail 1c. Thus, all three prongs 18c provide the turning lock function of the femur neck screw 10b, both in the femur nail 1c and in the bone fragment.

The underlying principle of the present invention can be transferred to locking elements with nails or plates with other applications in the surgical range. The design of the invention and its variants are indicated in the appropriate patent claims.

The invention claimed is:

1. An intramedullary nail system for fixation of fractures of a proximal femur, comprising:
   an intramedullary nail extending along a nail longitudinal axis and being sized and shaped for insertion into an intramedullary area of the femur, comprising:

a proximal end having a head with a borehole extending therethrough diagonal to the nail longitudinal axis, wherein the borehole includes one or more grooves; and a distal end having a shank with a diameter reduced with respect to a diameter of the head of the proximal end, wherein the shank has a cross hole and an axial notch;

a femur neck screw extending along a neck screw longitudinal axis, the neck screw comprising:

a cluster at a proximal end of the neck screw;

a plurality of longitudinal slots oriented in a direction of the neck screw longitudinal axis; and a threaded end at a distal end of the femur neck screw; and a locking element having a plurality of prongs arranged substantially parallel to the neck screw longitudinal axis, a thickness of each of the prongs of the locking element, measured in a radial height direction (h), increasing toward a distal end of each of the prongs, at least one prong of the locking element being inserted into a corresponding one of the longitudinal slots and expanding to an expanded condition in which a proximal end of the at least one prong is further from the neck screw longitudinal axis than the proximal end of another one of the prongs wherein, in the expanded condition, the proximal end of the at least one prong is received within one of the grooves of the borehole of the femur nail, the distal end of at least one of the prongs being received in a corresponding slot of the neck screw to form a twisting lock between the neck screw and the nail by a positive connection between the locking element and the nail, and between the locking element and the femur neck screw.

2. An intramedullary nail system according to claim 1, wherein at least two axial longitudinal slots and at least two prongs are provided.

3. An intramedullary nail system according to claim 1, wherein the grooves are arranged in the borehole of the femur nail in a number and position corresponding to the longitudinal slots in the femur neck screw.

4. An intramedullary nail according to claim 1, wherein the locking element includes more prongs than grooves in the borehole of the femur nail, and wherein at least one prong in a groove in the borehole of the femur nail and at least one prong, preferably the same prong, of the femur neck screw is guided in a longitudinal slot.

5. An intramedullary nail system according to claim 1, wherein the depth of the longitudinal slots in the femur neck screw decreases toward the distal end.

6. An intramedullary nail system according to claim 1, wherein the depth of the individual longitudinal slots is different.

7. An intramedullary nail system according to claim 1, wherein the increase in the thickness of the prongs is gradual.

8. An intramedullary nail system according to claim 1, wherein the number of longitudinal slots exceeds the number of prongs of the locking element.

9. An intramedullary nail system according to claim 1, wherein the prongs of the locking element are evenly arranged over the locking element length.

10. An intramedullary nail system according to claim 1, wherein the prongs of the locking element are unevenly arranged over the locking element length and the prongs are substantially V, X or Y-shaped.

11. An intramedullary nail system according to claim 1, wherein the locking element has three prongs.

12. An intramedullary nail system according to claim 1, wherein the prongs of the locking element at their proximal end are connected by a circular collar.

13. An intramedullary nail system according to claim 1, wherein a safety element is provided for axial safety of the locking element.

14. An intramedullary nail system according to claim 13, wherein the safety element is designed as a mounting screw threaded by a collar into the proximal end of the femur neck screw.

15. An intramedullary nail system according to claim 1, wherein the femur nail, the femur neck screw, the locking element, and a safety element consist of titanium alloys and/or implant steel.

16. An intramedullary nail system according to claim 1, wherein the axial notches taper along the longitudinal axis.

17. An intramedullary nail system for fixation of fractures of a proximal femur comprising:

a intramedullary nail extending along a nail longitudinal axis, comprising:

a proximal end having a head with a borehole extending therethrough diagonal to the nail longitudinal axis, wherein the borehole includes a plurality of grooves; and a distal end having a shank with a diameter reduced with respect to a diameter of the head of the proximal end, wherein the shank has a cross hole and an axial notch; and a femur neck screw extending along a neck screw longitudinal axis, the neck screw comprising:

a cluster at a proximal end of the neck screw;

a locking element having a plurality of prongs arranged substantially parallel to the neck screw longitudinal axis, a thickness of each of the prongs of the locking element, measured in a radial height direction (h), increasing toward a distal end of each of the prongs;

a plurality of longitudinal slots oriented in an axial direction, wherein the a plurality of longitudinal slots are evenly spaced apart; and a threaded end at a distal end of the femur neck screw, wherein a proximal end of at least one prong is received within one of the grooves of the borehole of the femur nail while the proximal end of the at least one prong is expanded further from the neck screw longitudinal axis than a proximal end of another one of the prongs, a distal end of the at least one prong being received in a corresponding slot of the neck screw to provide a turning lock function between the femur neck screw and the nail and between the locking element and the femur neck screw.

18. An intramedullary nail system according to claim 17, wherein the axial notches taper along the longitudinal axis.

* * * * *